United States Patent [19]
Chipperfield et al.

[11] Patent Number: 5,670,852
[45] Date of Patent: Sep. 23, 1997

[54] PUMP MOTOR AND MOTOR CONTROL

[75] Inventors: Keith E. Chipperfield; Kevin O'Hara; Greg Kangiser; Steve Soar, all of Vancouver, Wash.

[73] Assignee: Micropump, Inc., Vancouver, Wash.

[21] Appl. No.: 408,592

[22] Filed: Mar. 22, 1995

Related U.S. Application Data

[63] Continuation-in-part of Ser. No. 183,649, Jan. 18, 1994, abandoned.

[51] Int. Cl.$^6$ ............................................. H02P 1/00
[52] U.S. Cl. ........................ 318/280; 318/254; 318/138; 318/439
[58] Field of Search .......................... 318/254, 138, 318/439, 280, 286, 369; 60/325, 368

[56] References Cited

U.S. PATENT DOCUMENTS

| | | | |
|---|---|---|---|
| 3,883,785 | 5/1975 | Fulcher et al. | 318/314 |
| 4,015,154 | 3/1977 | Tanaka et al. | 310/42 |
| 4,283,665 | 8/1981 | Mizumoto | 318/317 |
| 4,475,073 | 10/1984 | Hawkins | 318/369 X |
| 4,605,884 | 8/1986 | Miyagi | 318/254 X |
| 4,712,853 | 12/1987 | Howard | 318/254 X |
| 4,922,604 | 5/1990 | Marshall et al. | 29/598 |
| 4,940,927 | 7/1990 | Fisher | 318/809 |
| 4,998,865 | 3/1991 | Nakanishi et al. | 417/423 |
| 5,173,631 | 12/1992 | Suganuma | 318/138 X |
| 5,311,107 | 5/1994 | Shimegi et al. | 318/254 X |
| 5,433,541 | 7/1995 | Hieda et al. | 318/254 X |
| 5,495,161 | 2/1996 | Hunter | 318/254 X |

*Primary Examiner*—Karen Masih
*Attorney, Agent, or Firm*—Klarquist Sparkman Campbell Leigh & Whinston, LLP

[57] ABSTRACT

A pump motor controller for making pump motor speed independent of fluid pressure at the inlet and outlet of the pump. A first embodiment employs feedback to cause pump motor speed to converge to a desired speed established with a reference input signal. Based on this feedback, forward and reverse drive amplifiers in the first embodiment cause the pump motor speed to track the desired speed. A second embodiment employs a controller that produces drive signals to a stepper motor in proportion to a reference frequency. The controller and stepper motor in the second embodiment achieve speed control at low speeds without the use of a feedback control loop.

16 Claims, 8 Drawing Sheets

PUMP MOTOR AND MOTOR CONTROL

REFERENCE TO PARENT CASE

This is a continuation-in-part of patent application Ser. No. 08/183,649 to Keith E. Chipperfield, entitled "PUMP MOTOR CONTROLLER," filed Jan. 18, 1994 abandoned, which is hereby incorporated by reference.

FIELD OF THE INVENTION

The invention generally relates to pump motors, and more specifically relates to an improved pump motor design including motor control for controlling flow rate in the presence of external pressures on the pump.

BACKGROUND OF THE INVENTION

Electrical pumps typically include a pump drive system to control the rate of flow through the pump by controlling the speed of a pump motor. While it is important in many applications to maintain tight control of the pump, external pressures can degrade pump performance. Specifically, pressure exerted by fluid at the inlet to the pump can actually force the pump motor to rotate faster than the desired speed in a phenomenon known as "turbining." Negative pressure at the pump outlet can also cause turbining, resulting in loss of control of fluid flow through the pump. It is therefore desirable to develop a pump motor controller that makes pump performance independent of fluid pressure at the inlet and outlet of the pump.

One method to control turbining is to use braking circuitry to negate the effect of fluid pressure on motor speed. For systems utilizing a brushless motor to drive the pump, braking may be achieved by either suspending commutation of the motor, or by presenting a low electrical impedance to the motor windings.

Commutation in a brushless D.C. motor consists of creating a rotating magnetic field in the motor's stator to exert magnetic forces on the rotor, causing it to rotate. This rotating field is established by sequentially applying current to windings arranged in the stator. When commutation of the motor is suspended, an electrical current is applied to only a single pair of windings in the stator. The magnetic field generated by the pair of windings brakes the rotor because it attempts to align itself with the magnetic field of the stator.

As a braking technique, suspended commutation in the motor has the disadvantages of producing high torque ripple and requiring significant amounts of current. Torque ripple is the fluctuation in torque applied to the rotor as it passes through a magnetic field of varying intensity and orientation. During suspended commutation, torque ripple is very pronounced because the rotor passes through a field, established by a sole pair of windings, that tends to force the rotor to a single position in opposition to the rotor's inertia. As a result, the motor does not rotate smoothly, but rather surges, causing uneven flow through the pump and placing added stress on the motor components. Suspended commutation also requires additional current reducing the efficiency of the pump drive. Because of these drawbacks, suspended commutation does not adequately address the turbining problem.

Another way to brake the pump motor to control turbining is to present a low electrical impedance to, or in other words "short," the windings of the stator. Shorting the stator windings has the effect of establishing an opposing magnetic field in the stator that resists motion of the rotor. The spinning rotor induces current to flow in the shorted windings, and the magnetic field generated from this current opposes the magnetic field of the spinning rotor. The current induced in the stator causes the motor to heat up as energy is dissipated in the resistance of the stator coils.

Controlling motor speed by shorting the stator windings has several disadvantages. First, it requires additional heat-sinking to dissipate the heat in the stator. Second, it requires expensive power switches to provide the low impedance path across the stator windings. Finally, under certain pressure conditions, it may not provide the degree of braking required to maintain control of the motor speed due to the finite impedance of the stator windings. Therefore, providing low impedance to the windings similarly fails to adequately address the turbining problem. Moreover, simply braking the pump motor to minimize the turbining problem does not achieve the ultimate goal of making motor speed, and thus pump performance, independent of external pressures on the pump.

The use of a pump motor in dialysis machines is one application where external pressures on the pump can make it difficult to control pump motor speed. In this context, positive inlet pressure often builds up on the pump motor. Pump motors and associated motor controllers used in this application do not adequately address this problem. For example, brushless D.C. motors have been used to control fluid flow in a dialysis machine, but they have not been used with effective control to address the problems relating to external fluid pressure.

The stepper motor is another type of motor used in dialysis applications, but for a different purpose than the brushless D.C. motor. Stepper motors are sometimes used to control the flow of small amounts of highly concentrated solution to another fluid such as water. This application takes advantage of the stepper motor's ability to provide improved positional control of the motor. The typical stepper motor has at least 20 teeth, and most commonly, around 200 teeth, to provide precision control of the rotor position. The number of teeth in the stator defines the degrees per step; for example, twenty teeth correspond to 18 degrees per step, and 200 teeth correspond to 1.8 degrees per step. While minimizing the degrees per step makes the stepper motor effective to precisely control the flow of small amounts of fluid, it is not suitable for other dialysis applications requiring high speed operation. The typical stepper motor cannot generate sufficient torque to operate at high speeds and also control fluid flow in presence of high inlet pressure.

In light of the foregoing, there is a need for a pump motor controller that more effectively prevents turbining and that provides for tighter motor speed control.

SUMMARY OF THE INVENTION

It is an object of the invention to provide a pump motor controller that more effectively addresses the turbining problem, and thereby overcomes the drawbacks of the braking methods described above.

Another object of the invention is to provide a pump motor controller that makes pump performance independent of external pressures on the pump.

Yet another object of the invention is to provide a pump motor controller allows for direct control of motor speed based upon a control frequency, regardless of pressures on the pump.

To achieve these objects, one embodiment of the invention provides a pump motor controller including a feedback loop to maintain pump motor speed independent of external pressures on the pump. The pump motor controller according to the invention includes commutation sensors, a comparator, and a drive circuit. The commutation sensors sense the position of the rotor to determine motor speed, and to facilitate commutation of the motor. The comparator, coupled to the commutation sensors and a reference input, produces an output signal based on the difference between pump motor speed and the reference input. The drive circuit receives the output signal of the comparator and drives the pump motor in forward or reverse depending on information provided in the output signal. From information such as the voltage of the output signal, the drive circuit determines the direction of commutation of the motor, forward or reverse, and the amount of current to be supplied to the motor for commutation. In sum, the pump motor controller forces motor speed to track the reference input by comparing the reference input to motor speed and adjusting motor speed accordingly.

The pump motor controller uses reverse commutation to decrease motor speed and to negate the turbining effect. When motor speed exceeds the reference input,, the drive circuit commutates the pump motor in reverse until the desired speed is achieved. Reverse commutation minimizes torque ripple and consumes less power than suspended commutation. Moreover, reverse commutation does not require expensive power switches or extensive heatsinking as does the technique of shorting the'stator windings to achieve braking. As a result, the pump motor controller according to the invention provides superior motor control without the drawbacks of prior braking techniques.

The pump motor controller may also include a frequency discriminator to stop the pump motor when the reference input falls below a threshold value. In some brushless motor applications, it is desirable to stop the motor at low frequencies because of the erratic performance due to torque ripple and low inertia of the rotor. A frequency discriminator according to an embodiment of the invention detects when the reference input drops below a threshold value and activates the driver circuit to provide reverse commutation of the pump motor. A reverse motion detector is then coupled to the commutation sensors and to the drive circuit to inhibit reverse commutation when the motor moves in reverse. The frequency discriminator, thus, improves pump performance by preventing the motor from operating at low speeds where performance of the pump motor is not acceptable.

A second embodiment of the invention provides improved motor control, even at low pump motor speeds. In this second embodiment, a pump motor controller provides control over the speed of a stepper motor in the presence of external pressures on the pump. The pump motor controller receives a reference frequency input signal and translates it to control signals that sequentially actuate drivers to stator windings of the stepper motor. By sequentially energizing windings of the stepper motor in proportion to the input frequency, the pump motor controller can maintain effective control over pump motor speed without the need for a feedback control loop.

The configuration of the stepper motor enables it to operate effectively over a wide range of speeds. In this second embodiment, the pump motor controller can operate the stepper motor at low speeds to maintain a low flow rate, and can also operate at higher speeds to enhance the utility of the pump motor. The second embodiment achieves this performance using only 6 stator teeth, corresponding to 60 degrees per step. This number of stator teeth provides for accurate low speed control, but also creates enough torque for the pump motor to operate effectively at higher speeds.

Further advantages and features of the invention will become apparent to those skilled in the art from the following description and accompanying drawings.

DETAILED DESCRIPTION

Figure 1:
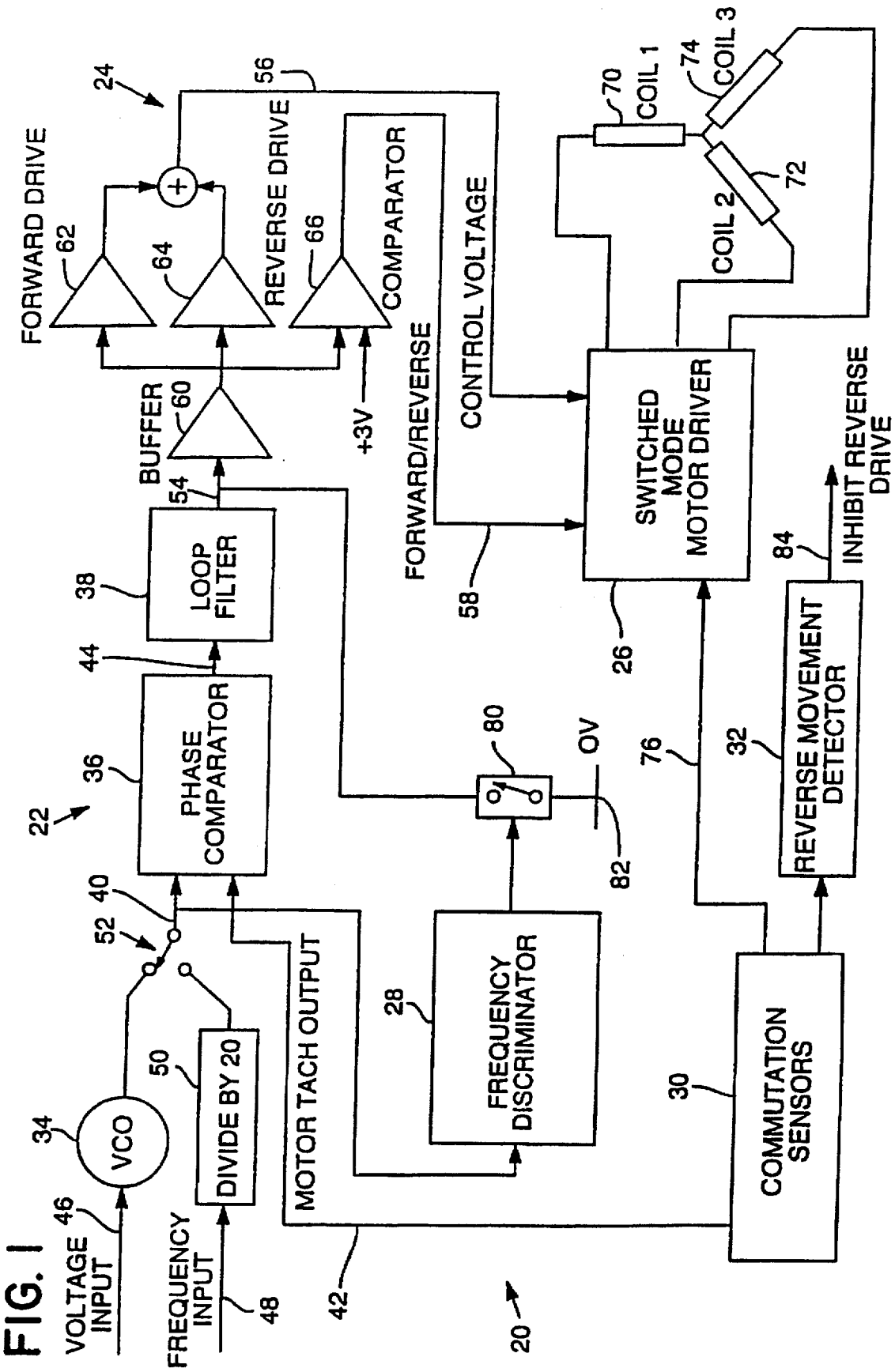
FIG. 1 illustrates a block diagram of a pump motor controller according to a first embodiment of the invention.

FIG. 1 illustrates a block diagram of a pump motor controller 20 according to a first embodiment of the invention. This embodiment of the pump motor controller includes the following primary components: 1) a phase locked loop circuit 22; 2) a drive circuit 24; a switch mode motor driver 26; 3) a frequency discriminator 28; 4) commutation sensors 30; and 5) a reverse movement detector 32.

The phase locked loop circuit 22 includes a voltage controlled oscillator (VCO) 34, a phase comparator 36, and a loop filter 38. The phase locked loop circuit 22 provides the function of comparing a reference input 40 with motor tach output 42 and providing an output signal 44 relating to the difference between pump motor speed and the reference input 40. The output signal 44 indicates whether the drive circuit should apply forward or reverse commutation to the pump motor and also indicates the amount of current to be supplied for commutation. In this embodiment, the output signal 44 is a switching output voltage, converted to a D.C. voltage by loop filter 38. Alternatively, the output signal could convey information regarding motor speed in the form of current, frequency, etc. Regardless of the form of this information, the drive circuit 24 interprets it and drives the pump motor in forward or reverse as necessary.

The reference input is either a voltage input 46, to control pump motor speed based on the magnitude of the voltage input, or a frequency input 48, to control motor speed based on the frequency of a square wave input. In the first instance, the VCO 34 converts the voltage input 46 to an oscillating digital signal having a frequency proportional to the magnitude of the voltage. In the latter instance, the frequency input 48 allows for the RPM of the motor to be directly controlled by a control frequency. In this embodiment, the frequency input 48 is adjusted by a divide by 20 circuit 50 to increase the range of the input frequency used to control motor speed. With the divide by 20 circuit, the RPM of the motor equals the input frequency divided by four for the particular configuration of a brushless D.C. motor described in more detail below.

The phase locked loop circuit includes a means for selecting 52 a voltage or frequency input. In this embodiment, a voltage or frequency input is selected simply by applying one input in the absence of the other. However, the pump motor controller may contain switching circuitry either as part of the phase locked loop circuit or as a discrete component or components to select the reference input 40 from at least one input control signal such as the voltage input 46 or frequency input 48 control signals.

The inputs to the phase comparator 36 are the reference input 40 and the motor tach output 42, fed back from the pump motor by the commutation sensors 30. The phase comparator 36 compares the phase of the motor tach output 42 with the reference input 40 and drives the comparator output 44 high if the phase of the reference input leads the phase of the motor tach output 42. Conversely, the phase comparator 36 drives the comparator output 44 low if the reference input 40 lags the phase of the motor tach output 42. A loop filter 38 then filters the switching output voltage 44 of the phase comparator to provide a steady D.C. voltage 54 to the drive circuit 24.

The phase locked loop circuit 22 provides feedback control of the pump motor such that pump motor speed tracks the desired speed conveyed by the reference input 40. It should be understood that the invention does not specifically require the use of a phase locked loop circuit for feedback control of pump motor speed. Other types of feedback control may be used, including, but not limited to, a frequency locked loop circuit, or feedback control loop based on voltage. In the former example, a frequency locked loop circuit would compare the motor tach output frequency with a reference input frequency. In the latter example, a voltage comparator would compare the motor tach output, converted to a voltage, with a reference input voltage. In each case, a comparator would provide an output signal to the drive circuit based on a comparison of the motor speed and a reference input.

In this embodiment, the level of the output voltage 54 of the loop filter 38 reflects whether motor speed must be increased or decreased to make the motor speed converge with the reference input 40. When motor speed is less than the reference input, the output voltage 54 ranges from three to six volts, and when the motor speed exceeds the reference input 40, the output voltage 54 ranges from zero to three volts. An output voltage increasing from three to six volts represents increasing forward drive, and conversely, an output voltage decreasing from three volts to zero represents increasing reverse drive.

Coupled to the output of the loop filter 38, the drive circuit 24 receives the output voltage 54 from the loop filter 38 and provides both a control voltage 56 and forward/reverse drive directional signal 58 to the switch mode motor driver. The drive circuit 24 includes a buffer 60, a forward drive amplifier 62, a reverse drive amplifier 64, and a comparator 66. The buffer 60 receives the output voltage 54 from the loop filter 38 and serves to prevent loading of the filter 38 and to provide isolation for the drive amplifiers 62, 64, 66. When the output voltage 54 exceeds three volts, the forward drive amplifier 62 produces a control voltage 56 ranging from zero to approximately five volts. Similarly, when the output voltage 54 is below three volts, the reverse drive amplifier 64 produces a control voltage 56 ranging from zero to about five volts. In the case of forward and reverse drive, the control voltage 56 is proportional to the absolute value of the difference between output voltage 54 of the loop filter 38 and three volts. The comparator 66 of the drive circuit 24 compares the output voltage with a three volt reference and then provides a forward/reverse directional signal 58, specifying forward or reverse drive. In this embodiment, the directional signal is either a logic high signal, representing forward drive, or a logic low signal, representing reverse drive.

A switch mode motor driver 26 is coupled to the drive circuit 24 and to commutation sensors 30. The drive circuit 24 provides a D.C. control voltage 56 and forward/reverse directional signal 58 to the switch mode motor driver 26. In response, the motor driver 26 provides current to coils 1, 2, and 3 (70, 72, 74) to commutate a D.C. brushless motor in forward or reverse at a speed proportional to the control voltage. To control commutation, the motor driver 26 employs electronic switching to selectively energize coils 1, 2, and 3 (70, 72, 74) of the stator of the pump motor.

The pump motor controller 20 is designed for a three phase brushless D.C. motor, but the specific configuration of brushless D.C. motor is not critical to the invention. Variations in the configuration of the pump motor may include either a bipolar or unipolar drive, a rotor magnet having two, four, or more poles, and a stator having any number of stator teeth upon which the stator coils (70, 72, 74) are wound. Bipolar drive allows current to be applied bi-directionally to the stator coils, and thus, is particularly useful in energizing pairs of coils simultaneously to generate more torque. Increasing the number of poles in the rotor and the number of stator teeth can also improve performance of the motor by reducing torque ripple.

The motor configuration to be used with pump motor controller 20 specifically is a three phase brushless D.C. motor with bipolar drive. The stator includes six teeth for mounting the three stator coils. The coils are divided in half and are each mounted upon two stator teeth arranged 180 degrees apart. Finally, the rotor includes a permanent magnet with four poles. To eliminate the need for motor shaft bearings and seals in the pump, the rotor and drive shaft may be located in a separate, enclosed cavity from the stator. Such an integrated pump and motor assembly is described in more detail in U.S. Pat. Nos. 5,096,390 and 5,197,865, which are hereby incorporated by reference.

The foregoing pump motor and pump assembly serves as an example of aspects of a pump drive system to be used with the pump motor controller of the invention. The switch mode driver 26 and commutation sensors 30 provide the interface between the pump motor controller 20 and the pump motor; however, the pump motor and pump assembly are not part of the pump motor controller 20.

Returning now to the description of the pump motor controller 20 of FIG. 1, commutation sensors 30, arranged adjacent the stator in the pump motor, sense the position of the rotor and provide a logic high signal 76 when rotor passes each sensor. The commutation sensors 30 are coupled to the phase comparator to provide the motor tach output 42. The commutation sensors 30 are also coupled to the switch mode motor driver 26 to communicate the rotor's position to the motor driver 26. Finally, the commutation sensors 30 are coupled to a reverse movement detector 32, used in stopping the motor.

The pump motor controller 20 includes a frequency discriminator 28 to enable the controller 20 to stop the pump motor when the reference input frequency 40 becomes too low. In some brushless motors, it may be necessary to stop the motor when the frequency of the reference input 40 drops below a threshold value because the physical limitations of the motor may substantially degrade performance. Specifically, the low inertia of the rotor coupled with the use of fewer stator teeth make it difficult to maintain a smooth motor speed at a low RPM. To avoid this problem, the motor may be stopped when the reference input 40 drops below a threshold value.

Accordingly, the frequency discriminator 28 senses when the input frequency drops below a threshold value and actuates a switch 80, pulling the output voltage of the loop filter 54 to ground 82. The resulting low voltage input to the drive circuit causes the drive circuit 24 to provide full reverse drive until the rotor physically reverses direction. The reverse movement detector 32 then disables the reverse drive amplifier to stop the pump motor.

When the reverse movement detector 32 detects reverse rotation of the rotor in the pump motor, it provides a signal 84 to the reverse drive amplifier 64, effectively turning it off. During the process of stopping the motor described above, the pump motor controller 20 applies reverse commutation until the motor actually begins to operate in reverse. The reverse movement detector 32 detects the first instance of reverse rotation and then turns off the reverse drive amplifier 64. If fluid pressure on the pump (turbining) forces the rotor forward, the pump motor controller 20 applies reverse commutation again until the rotor moves in reverse. In some instances, the rotor may oscillate, forced forward by external fluid pressure and then driven in reverse by the pump motor controller 20. For moderate external fluid pressures, the rotor stops as the attractive forces of the rotor to a stator tooth overcomes the turbining effect forcing the rotor forward. For high pressures, the rotor continues to oscillate, but control of fluid flow through the pump is sufficiently maintained despite the high pressure tending to force the rotor forward.

To summarize, the pump motor controller 20 maintains control of pump motor speed with a feedback loop. The feedback loop enables the pump to perform independently of positive fluid pressures at the inlet and negative fluid pressures at the outlet of the pump. This implementation uses a phase locked loop circuit 22 to compare the motor tach output 42 with a reference input 40. The phase locked loop circuit 22 provides information to a driver circuit 24 to either increase or decrease speed such that the motor tach output 42 converges to the reference input 40. Increasing forward drive results in faster forward commutation of a brushless D.C. motor, while increasing reverse drive results in faster reverse commutation of the motor. Reverse commutation is used to smoothly brake the motor for decreasing motor speed and for negating the turbining effect.

The pump motor controller 20 contains a frequency discriminator 28 and a reverse movement detector 32 used in stopping the motor. When the reference input 40 falls below a threshold value, the pump motor controller 20 provides full reverse drive until the motor physically reverses direction. When the motor moves in reverse, the reverse movement detector 32 inhibits the reverse drive amplifier 32 to stop the motor.

Figure 2:
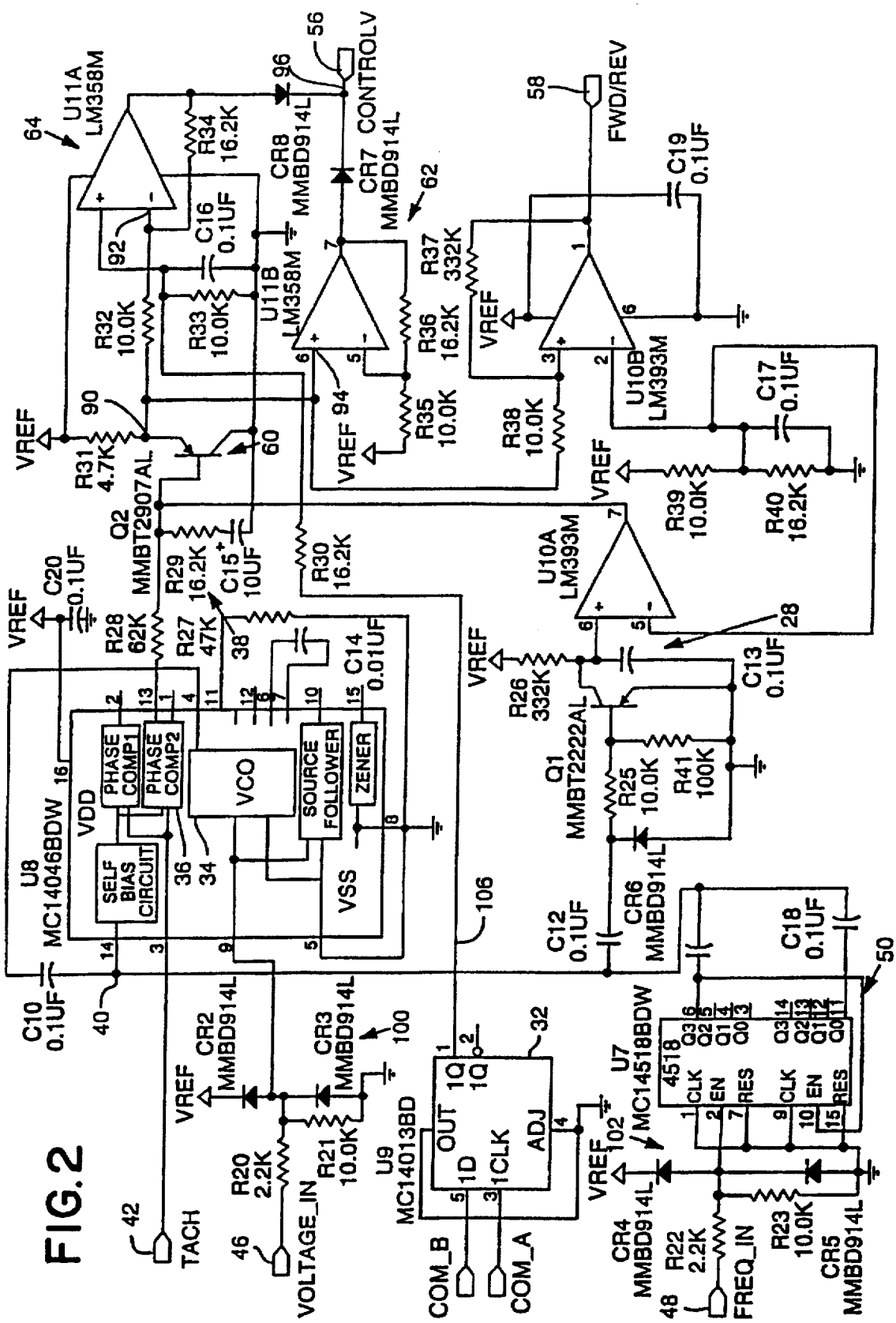
FIGS. 2 and 3 illustrate a schematic diagram of the pump motor controller of FIG. 1.
Figure 3:
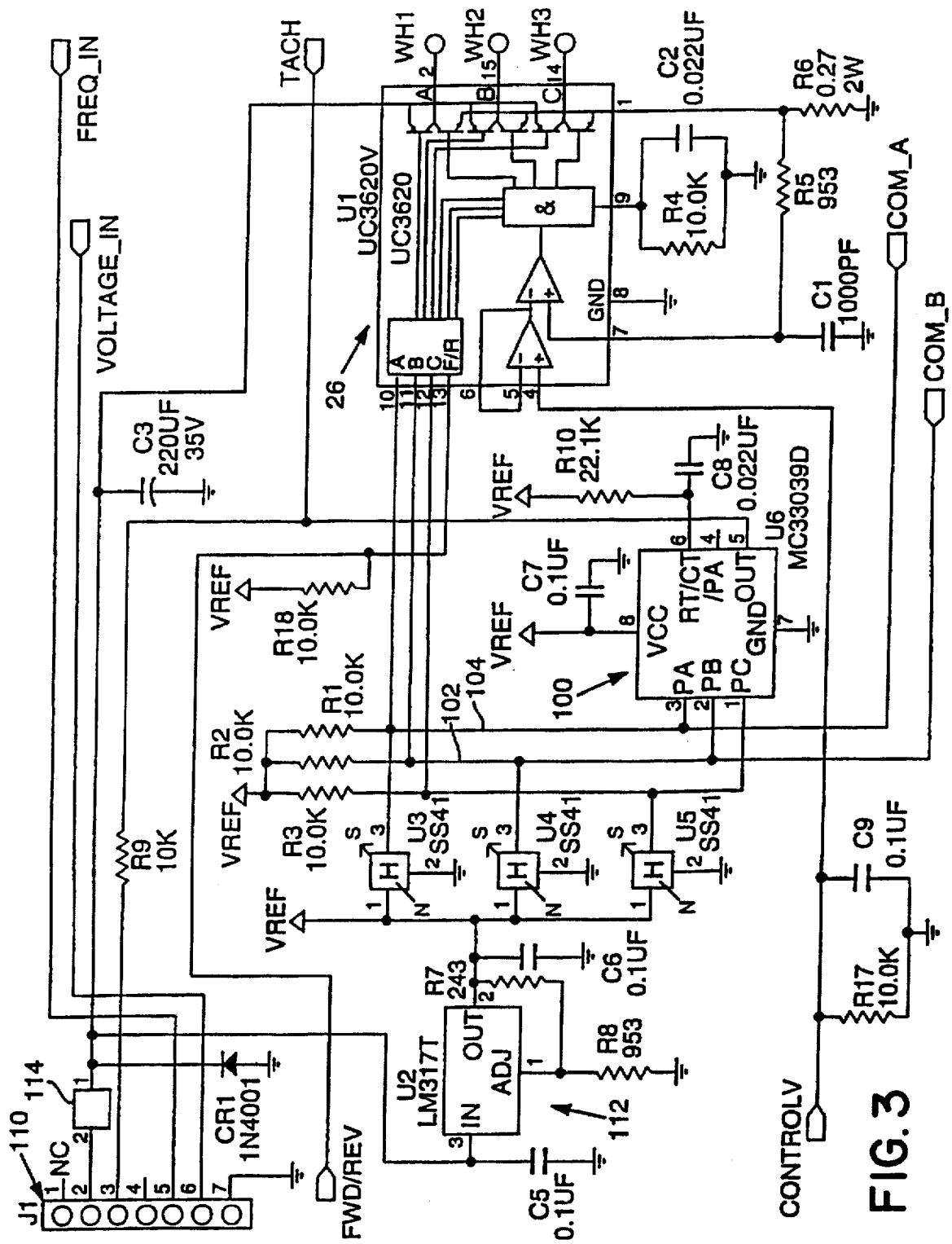

FIGS. 2 and 3 illustrate a schematic diagram of the pump motor controller 20 of FIG. 1. Each of the components illustrated in FIG. 1 and described generally above are shown in the schematic in greater detail.

Referring now to FIG. 2, the two inputs used to control motor speed are the voltage input 46, VOLTAGE_IN, and a signal oscillating at a control frequency 48, FREQ_IN. Both the voltage 46 and frequency input 48 signals pass through input protection circuitry 100, 102. The input protection 90 for the voltage input includes resistors R20 and R21, and diodes CR2 and CR3, while the input protection 92 for the control frequency signal includes resistors R22 and R23, and diodes CR4 and CR5. The control frequency signal 48 is coupled to a divide by 20 circuit 50, including two counters in a single chip, U7, and a capacitor C18 shown in FIG. 2. This implementation includes two decade counters from a MC14518BDW chip, commercially available from Motorola, Corporation; the first clock divides the input frequency by 10 and the second clock receives the output of the first clock and further divides the input frequency by 2.

The phase locked loop circuit 22, including the VCO 34, phase comparator 36 and loop filter 38 are shown in FIG. 2. The VCO 34 and phase comparator 36 are each part of a commercially available phase locked loop circuit chip, U8, from Motorola Corporation. The voltage input is coupled to the VCO 34 to be converted to an oscillating digital signal with frequency proportional to the magnitude of VOLTAGE_IN. The inputs to the phase comparator 36 are the motor tach output, TACH, (42) and the reference input. The reference input 40 is either the output of the VCO, VOLTAGE_IN converted to an oscillating signal, or the frequency input, FREQ_IN divided by 20.

The function of switch 52 is performed by the phase locked loop chip, U8, and capacitors C10 and C18. Both the output of the VCO 34 and the divider, U7, (50) are connected to the input of the phase comparator 36 via capacitors C10 and C18, respectively. If no frequency input is connected, the output of the divider, U7, (50) is static, and the voltage input can pass to the phase comparator via C10. If no voltage input is connected, then R21 pulls this input to ground, the VCO 34 stops oscillating, and the frequency input signal at the output of the divider passes to the comparator via C18. In this manner, the pump motor controller allows for selection of either the voltage or frequency input.

The loop filter 38, coupled to the output of the phase comparator 36, comprises resistors, R28 and R29 and capacitor C15. The loop filter 38 converts the switching output of the phase comparator 36 to a D.C. voltage ranging from zero to six volts.

The drive circuit 24 including the buffer 60, forward and reverse drive amplifiers 62, 64, and the comparator 66 of the drive circuit are illustrated in more detail in FIG. 2. The buffer 60 is transistor Q2, a standard bipolar junction transistor. The forward and reverse drive amplifiers 62, 64 each include an op amp from a dual op amp package LM358M, commercially available from Motorola Corporation. The reverse drive amplifier includes resistors R32, R33, and R34, op amp U11A, and diode CR8. The output of the buffer 90 is coupled to the negative input 92 of op amp U11A such that the reverse drive amplifier 64 inverts the output of the phase locked loop circuit. The reverse drive amplifier 64 receives voltages from approximately 3 to 0 volts and produces an output voltage from 0 to about 5 volts. The forward drive amplifier 62 includes resistors R35 and R36, op amp U11B, and diode CR7. The output of the buffer 90 is also coupled to the positive input 94 of the op amp U11B. The forward drive amplifier 62 is a non-inverting amp, receiving voltages from approximately 3 to 6 volts and producing an output of 0 to about 5 volts. Coupled together at the anodes 96 of diodes C7 and C8, the forward and reverse drive amplifiers provide the control voltage signal, CONTROL_V (56), to the switched mode motor driver 26.

The comparator 66 of the drive circuit includes an analog comparator, U10B, from a dual comparator package LM393M, resistors R37 and R38, and capacitor C19. Comparator U10B produces a high logic signal representing forward drive when the output of the phase locked loop circuit 22 exceeds three volts. Conversely when the output is below three volts, U10B produces a low logic signal representing reverse drive. The comparator of the drive circuit thus provides the directional signal, FWD/REV (58), to the switched mode motor driver.

The switched mode motor driver, U1, (26) is shown in more detail in the schematic diagram of FIG. 3. Commercially available from Unitrode Integrated Circuits of Merrimack, N.H., the switched mode motor driver, U1, (26) is a UC3620 Switched Mode Driver for Three Phase Brushless Motors. The motor driver 26 receives the control voltage, CONTROL_V, and directional signal, FWD/REV, from the drive circuit and provides currents to coils 1, 2 and 3 through ports WH1, WH2, and WH3, to provide for forward or reverse commutation of a brushless D.C. motor.

Commutation sensors 30, used to sense the position of the motor and to determine the motor tach output, are shown in detail in FIG. 3. Three Hall sensors, U3, U4, U5, sense the position of the rotor and provide a logic high signal each time a magnetic pole on the rotor passes in proximity to the sensor. The output of all three of the Hall sensors is also coupled to a MC33039 Closed Loop Brushless Motor Adaptor 100 commercially available from Motorola, Corporation. The motor adaptor, U6, (100) receives the digital signals from the sensors and provides the motor tach output. Additionally, the outputs 102, 104 of two of the Hall sensors are coupled to the reverse movement detector 32, a D flip-flop MC14013BD from Motorola Corporation, shown in FIG. 2.

The D flip-flop acts as a reverse movement detector by producing a voltage output 106 when the signal from Hall sensor corresponding to coil 2, COM_B, precedes the signal from Hall sensor corresponding to coil 1, COM_A. The signal, COM_A, serves as the clock on the flip flop and the signal, COM_B, serves as the D input. When the rotor moves in reverse, the sensor of coil 2 presents a low logic signal to the D input, and the sensor of coil 1 presents the clock signal, resulting in a low logic signal at the output of the D-flip flop. The output of the D-flip flop is coupled to the op amp, U11A, of the reverse drive amplifier 64. A low logic signal from the D-Flip flop 32 turns the reverse drive amplifier 64 off. As such, when the motor begins to remove in reverse, the pump motor controller 20 responds by turning off the reverse drive amplifier 64. The act of stopping the motor is thus completed when reverse commutation forces the motor to move in reverse.

The frequency discriminator 28 and switch 80 of FIG. 1 are shown in more detail in the schematic diagram of FIG. 2. The components of the frequency discriminator 28 are a comparator, U10A, from the dual comparator chip also used in the comparator of the drive circuit, a transistor Q1, capacitors C12 and C13, a blocking diode CR6, and resistors R25, R26, and R41. The reference input 40 is the input to the frequency discriminator 28 at C12. The reference input 40 is either the output of the VCO or a control frequency, FREQ_IN divided by 20. When the frequency of the reference input 40 is sufficiently high, transistor Q1 repeatedly discharges capacitor C13 to ground, and the resulting comparator is "off" with no impact on the drive circuit 64. However, when the frequency of the reference input 40 is below a threshold, approximately 30 Hz, capacitor C13 is able to charge up sufficiently to switch the output of the comparator, U10A, to approximately zero volts. When zero volts is presented at the buffer, Q2, the reverse drive amplifier 64 produces its maximum output, translating to full reverse drive.

Finally, FIG. 3 illustrates a connector 110 and voltage regulator 112 of the pump motor controller 20. The connector, J1, (110) provides for external connection to the pump motor controller 20. The second port of the connector is coupled to a fuse 114 used to protect the switched mode motor driver, U1, (26) and pump motor. The fuse 114 is also coupled to a voltage regulator circuit 112 including voltage regulator U2, capacitors C5 and C6, and resistors R7 and R8. The voltage regulator circuit 112 provides a 6.2 volt reference voltage, $V_{REF}$, to the circuitry of the pump motor controller 20.

Though a first embodiment of a pump motor controller has been described in detail above, it should be understood that the invention is not limited to this embodiment. For example, the feedback control need not be provided by a phase locked loop circuit. Other forms of feedback control, such as a frequency locked loop, may be used in place of the phase locked loop circuit. Similarly, the output signal of this feedback control need not be a D.C. voltage, conveying drive information to the drive circuit. Rather, such information may be provided through a control frequency or current, for example. Generally, where integrated circuit chips have been employed, discrete components could be used.

For some pump motor applications, it is critical that the pump motor maintain flow rate at or close to zero. This is especially difficult in the presence of external pressure on the pump that tends to force fluid through the pump. In these applications, the pump motor requires effective motor control at low pump motor speeds to negate the effect of external pressures.

Figure 4:
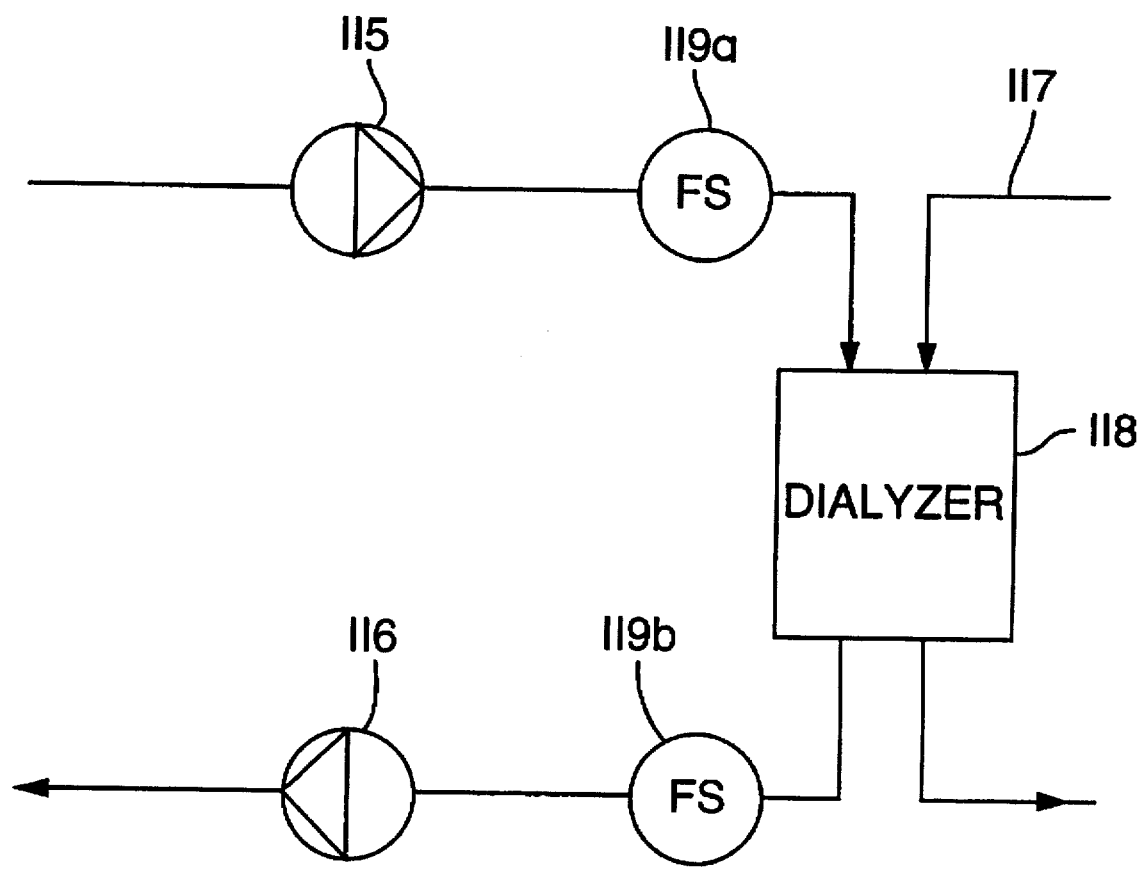
FIG. 4 illustrates a dialysis application utilizing dialysate pumps.

One application where this control over flow rate is particularly critical is in dialysis applications. FIG. 4 illustrates a dialysis application utilizing two dialysate pump motors 115, 116 to control flow through a dialyzer used to extract waste products from the blood. On one side 117, blood flows from the patient, through the dialyzer 118, and back to the patient. On the other side, the pumps 115, 116 control the flow of fluid through the dialyzer 118, and two flow sensors 119a, 119b measure flow rate on each end of the dialyzer 118.

To draw fluid from the blood, the first pump motor's (115) speed can be slowed or even stopped relative to the second motor's (116) speed. Operating the pump motors at different speeds enables the dialysis machine to draw excess fluid from the blood. Unfortunately, it also causes inlet pressure to build up at the first pump motor 115. This pressure can become great enough to force fluid through the pump motor 115. For a pump motor to effectively operate at low speeds, it must be able to control flow rate through the pump in the presence of the high inlet pressure.

A brushless D.C. motor does not adequately solve the problems caused by external pressure on a pump without resort to additional control circuitry. As described above in the context of the dialysis application, it is sometimes necessary to entirely block flow through a pump in the presence of high inlet pressure. To block flow with a positive inlet pressure, the pump motor must be operated in reverse at a slow speed or stopped entirely.

A brushless D.C. motor cannot operate effectively at slow speeds because it will ultimately stall when a controller attempts to drive the pump motor too slowly. A brushless D.C. motor requires that a back EMF be generated to produce torque on the rotor. At low speeds, back EMF generation is limited, and hence, so is braking torque. As a consequence, it is not possible to effectively control the speed of a brushless D.C. motor to maintain a low flow rate through the pump.

A second embodiment provides an alternative to the brushless D.C. motor to achieve improved performance at low speeds. A stepper motor control according to the second embodiment can effectively maintain a low flow rate in the presence of high inlet pressure.

Figure 5A:
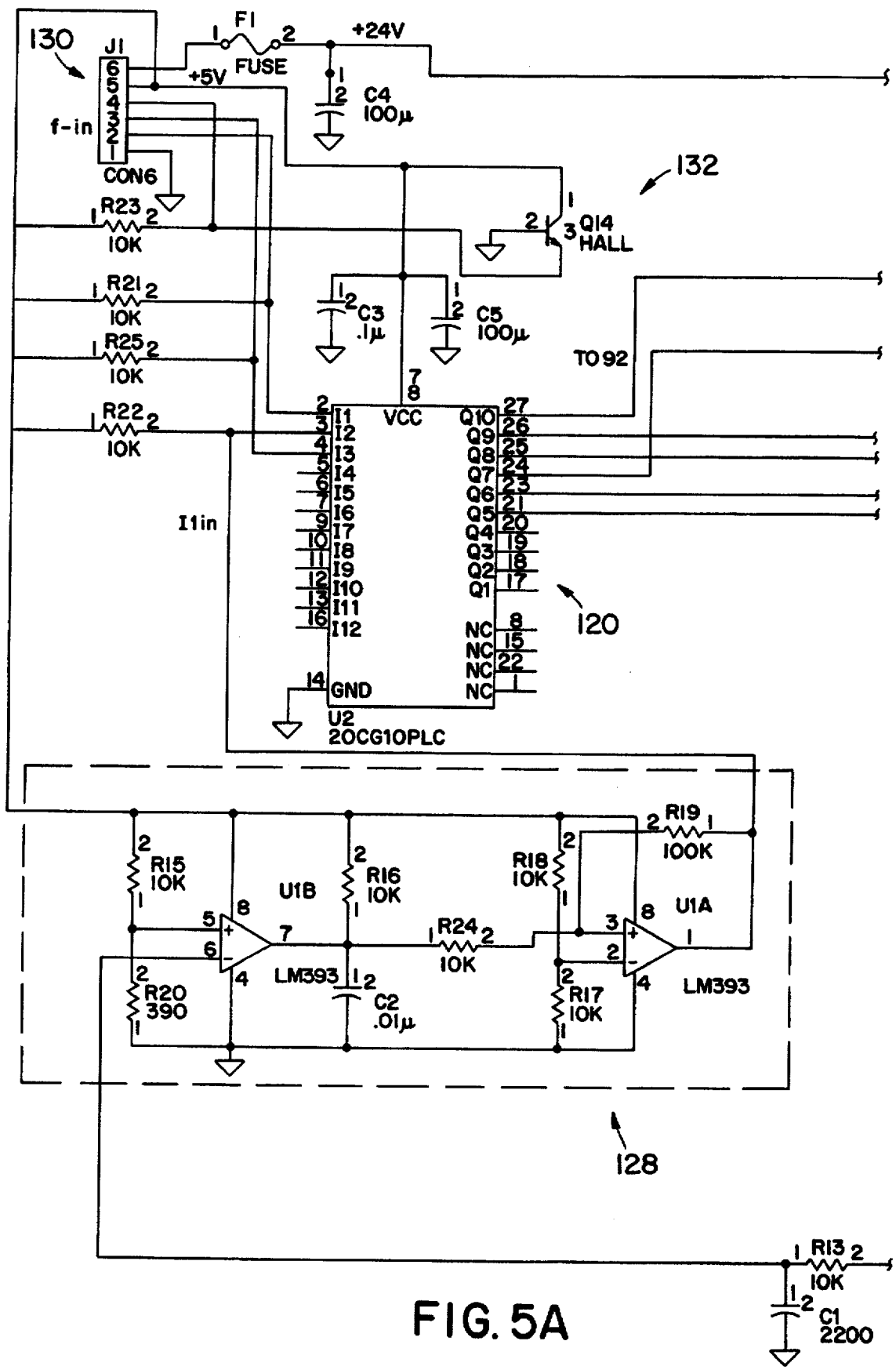
FIG. 5 illustrates a schematic diagram of a pump motor controller according to a second embodiment of the invention.
Figure 5B:
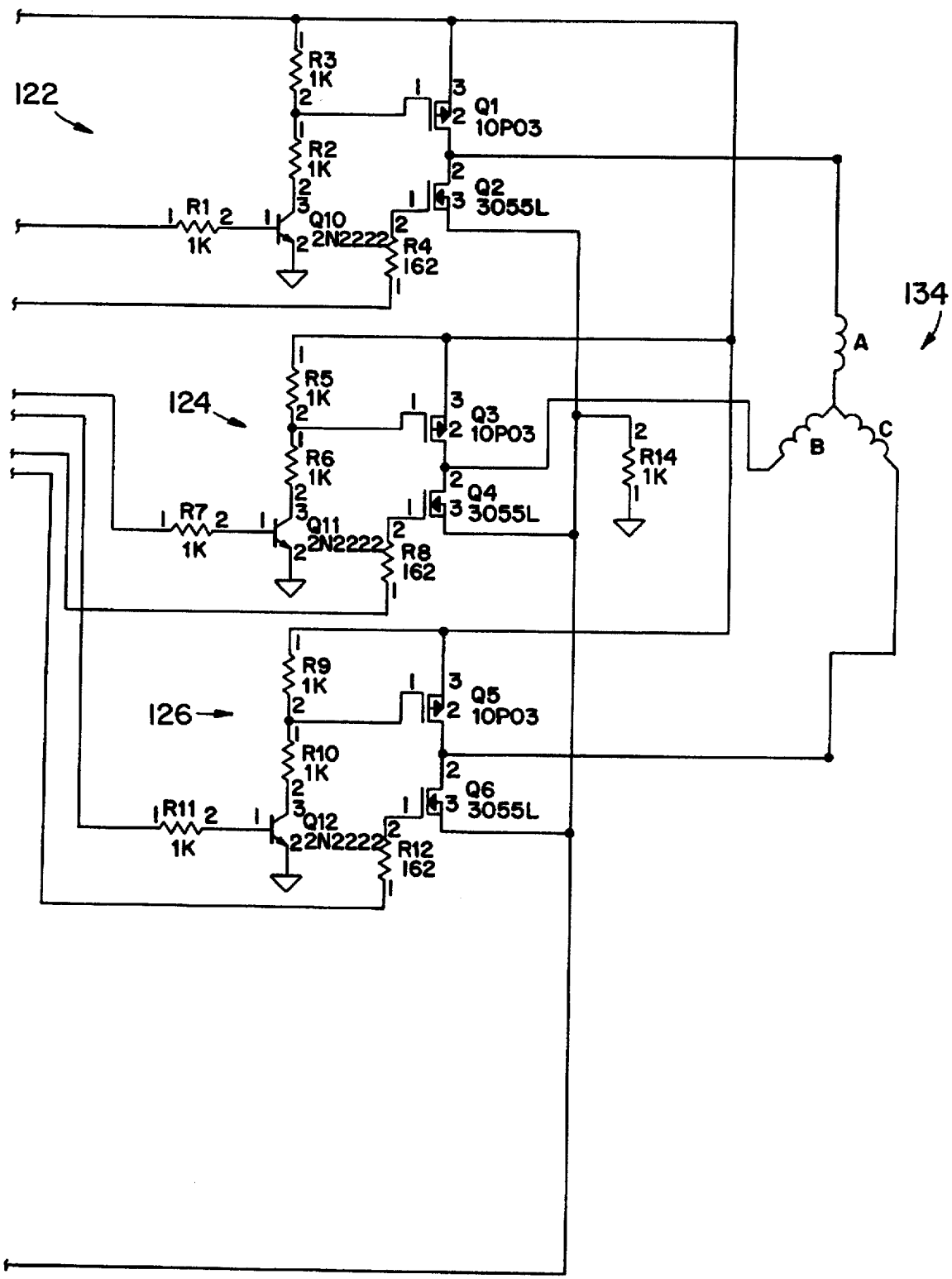

FIG. 5 illustrates a pump motor controller according to a second embodiment of the invention. The pump motor controller includes a controller 120, drivers 122, 124, 126 and current limiter circuit 128. The pump motor controller receives a reference input frequency and translates this reference input to control signals for a stepper motor. Through these control signals, the pump motor controller controls the flow of current to windings in the stator of the stepper motor. The controller applies current to the stator windings in a sequence such that the movement of the rotor closely tracks the movement of the magnetic field in the stator windings. Because of the close relationship between the timing of the control signals and the position of the rotor, the controller is able to control motor speed even at low speeds without a feedback control loop.

The pump motor controller has six terminals, all coupled through the connector, J1 (130). J1 is a standard connector and allows for external connection of the pump motor controller. The six terminals are TTL compatible and are defined as follows. Pin 1 is the ground pin, and Pin 5 is a 5 volt supply with expected current draw of less than 50 mA. Pin 6 is a 24 volt supply, and is fused at 3 Amps by fuse F1. Expected current draw from Pin 6 ranges from 0.7 A to 1.3 A, depending on load and speed. Current through Pin 6 is not linearly proportional to the applied load.

Pin 2 is the input pin for the reference frequency signal that controls pump motor speed. When no signal is applied to Pin 2, it is pulled up to 5 volts with a 10 K ohm resister, R21, for noise immunity. To start the pump motor or when reversing motor direction, the reference frequency input must be ramped up. In this implementation, the controller 120 is programmed such that the frequency of the reference input translates to a revolution output according to the equation: RPM Pump=5, Frequency In.

Pin 3 is the direction pin, enabling external control of the direction of fluid flow through the pump. A logic high and low signal at Pin 3 correspond to opposite directions of the pump motor. When no signal is applied to Pin 3, it is pulled up to 5 volts with a 10 k Ohm resistor, R25, for noise immunity.

Pin 4 is coupled to circuitry for confirming rotation of the pump motor. To indicate rotation, Pin 4 is coupled to a Hall sensor, Q14 (132). When the pump motor is not rotating, the signal on Pin 4 is pulled up to 5 volts through the 10 k Ohm resistor, R23. When the pump motor is rotating, the output at Pin 4 is a square wave with a frequency proportional to the rate of rotation of the pump motor. Specifically, the RPM of the motor is 30*(frequency at Pin 4).

The controller 120 is a programmable array logic (PAL) device programmed to provide step control to the three-phase, six winding stator of the stepper motor. This particular PAL is a 20CG10 PAL from Integrated Circuit Technologies, but a number of commercially available programmable devices can also be used. In response to the reference frequency input signal, the controller produces six control signals that step a 3 phase stator winding through six states.

Attached as Appendix A, the program listings for the controller illustrate examples of how to program the controller 120 to implement the control signals. As shown in Appendix A, the controller 120 implements a 3-bit counter that steps through 6 states. The first program listing includes a state table describing which windings are energized as the counter steps through six states. The second program listing includes instructions to implement forward and reverse direction control signals.

Referring to page 2 of Appendix A, the state table shows how the windings A, B, and C are energized during the six states. In the first phase, current flows into winding A and out of winding C. In the second phase, current flows into winding B and out of winding C. In the third phase, current flows into winding B and out of winding A. In the fourth phase, current flows into winding C and out of winding A. In the fifth phase, current flows into winding C and out of winding B. And finally in the sixth phase, current flows into winding A and out of winding B. In the second listing, the control signals implement reverse by swapping the states where current flows into windings A and C with the states where current flows out of A and C.

The controller directs current flow into the windings according to these 6 states by sending control signals to switch the drivers. The control signals actuate switches in the drivers to direct current flow through the windings.

The control signals are applied to a 3 phase stator winding 134 through drivers 122, 124, and 126. As shown in FIG. 5, each driver includes three resistors (R2, R3, R4; R5, R6, R8; and R9, R10 and R12), a bipolar transistor (Q10; Q11; and Q12), and a pair of MOSFETs (Q1,Q2; Q3,Q4 and Q5,Q6). When a control signal is applied to the bipolar transistor (e.g. Q10), Q1 turns on and current flows to Winding A. Conversely, when a control signal is applied to the gate of Q2, current flows from A. The control signals corresponding to each driver behave similarly to control the current flow through the windings.

The stepper motor includes the 3 phase, 6 winding stator as mentioned, and in addition has a rotor with a 4 pole magnet. The 6 windings in the stator are wound about 6 corresponding stator teeth. To form these 6 windings, Windings A,B, and C of FIG. 5 are each separated into two windings and wound about stator teeth positioned 180 degrees apart. In this configuration, the opposite pairs of windings are energized at the same time to maximize torque.

The use of only 6 teeth in a the stator is unique among stepper motors and provides improved performance. The typical stepper motor has more than 20 stator teeth (and less than 18 degrees per step), and sacrifices high speeds for better positional accuracy. However, in this implementation, the 6 teeth enables the motor to provide high speeds, ranging up to about 4000-5000 RPM, while still providing acceptable low speed control.

The stepper motor can maintain zero or very low flow rates in the presence of high external pressures on the pump motor. Specifically, the stepper motor controller is able to hold zero flow with positive inlet pressure by rotating the motor slowly in the reverse direction. For a given frequency, speed is precisely fixed. Therefore, even at a low speed, the pump motor controller can maintain a desired flow rate without the use of a local motor speed feedback control loop. The stepper motor can withstand in excess of 20 psi of inlet pressure while maintaining the rotor stationary. In this case, the pump motor controller receives a reference input signal having a frequency of zero Hz. If a low RPM is desired, the pump motor controller causes the rotor to rotate at a speed proportional to the frequency of the reference input ranging all the way to zero Hz. As such, the pump motor can be operated at a low RPM (e.g. from 0 to 50 RPM).

The pump motor controller includes a current limiter circuit 128. This current limiter comprises a monostable circuit having two LM393 comparators, U1A and U1B. The current limiter is designed so that the current flowing from the windings to ground is limited to 2.2 amps (This value varying with the resistance of the divider comprising R15 and R20). To achieve this, the monostable circuit produces a signal, Ilim, that effectively shuts off current to the windings for a pre-defined period of time. This period is set by the value of the resistor capacitor pair, R16 and C2.

The current limiter protects the windings by limiting the current flowing in them. In addition, the current limiter allows applications of high input voltage to rapidly increase the current in the coil being energized without excessive coil dissipation. By allowing higher input voltage, the current limiter enables the stepper motor to achieve higher speeds. In this case, the stepper motor can reach speeds ranging from 4000–5000 RPM.

While the second embodiment is explained in the context of a detailed example, it should be understood that the invention can be varied without departing from the scope of the invention. For example, the configuration of the stator windings could be altered; it is not necessary to use precisely six teeth, or to use a 3-phase, Y configuration. Two or four pole rotor magnets can be used. In addition, other circuit components could be used to implement the same counter function of the PAL, the same current limiting function of the monostable, or the same switching function of the drivers for the windings.

As noted, an illustrative application for motor control systems of the type described herein is an integrated pump/motor assembly as shown in U.S. Pat. Nos. 5,096,390 and 5,197,865. The assemblies shown in these patents can be improved somewhat, as set forth in the following discussion.

Each of the cited patents discloses an assembly that relies on a fluid-tight cup enclosure (reference numeral 54 in the patents) to isolate the stator windings from the fluid being pumped. While advantageous in many respects (e.g. eliminating the need for dynamic bearing seals), this cup enclosure is problematical. For one, it is fabricated by an expensive deep drawn method (i.e. hammer-molding into successively larger dies, with intermediate annealing steps), adding considerably to the cost of the final unit. Further, the cup spaces the rotor and stator further apart than can be achieved by applying the concepts of the invention. The air gap resulting from this prior art design reduces motor torque and efficiency.

Figure 6:
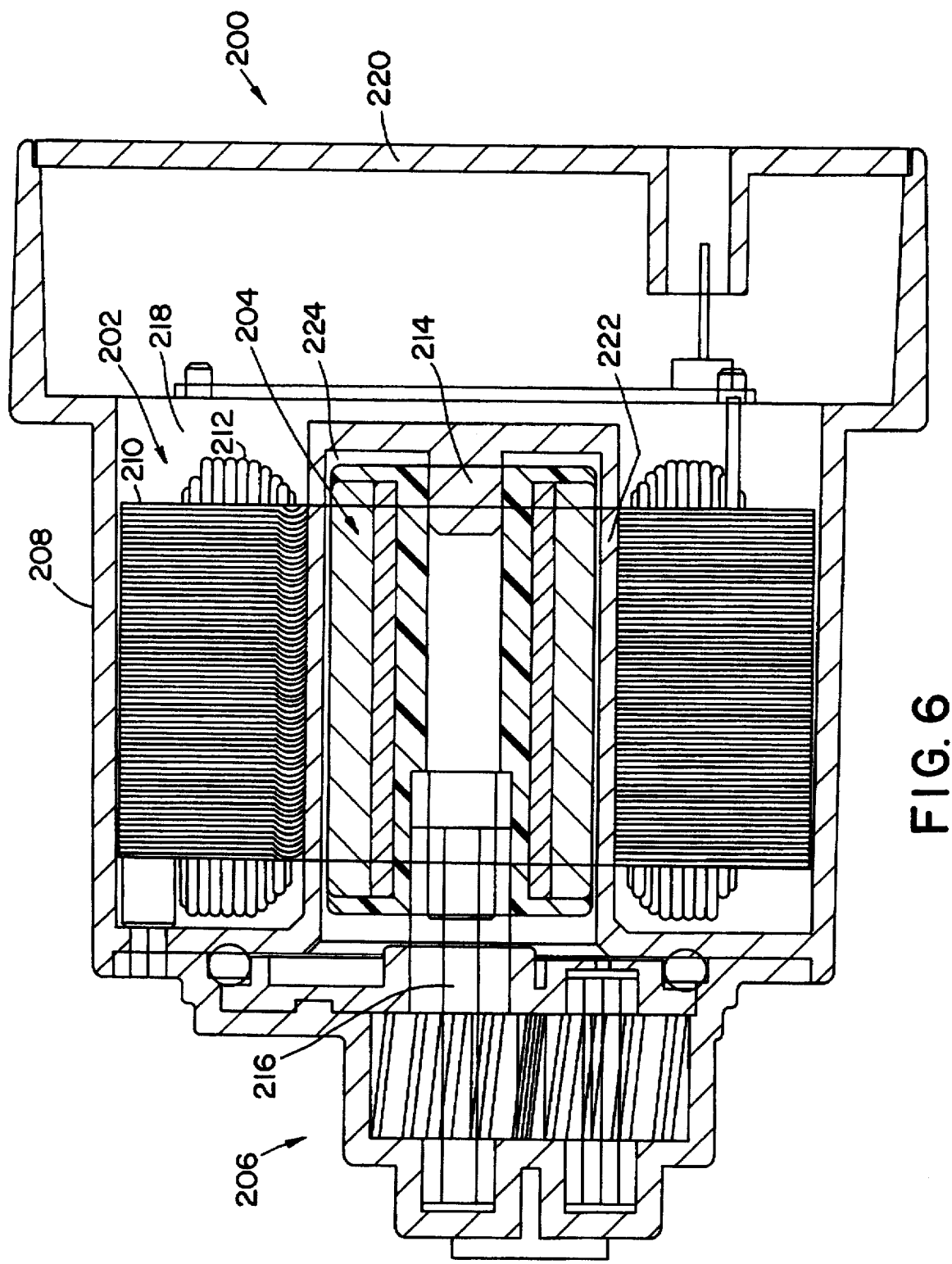
FIG. 6 shows an improved motor/pump assembly according to an embodiment of the invention.

FIG. 6 shows a first motor/pump assembly 200 that improves on the prior art design. The illustrated assembly includes a stator 202, a rotor 204, a gear pump head 206, and a molded housing 208.

The stator 202 is conventional and includes iron plate laminations 210 about which the 6 electromagnets 212 are wound. The rotor 204 is also conventional and comprises a radially-poled neodymium magnet (4 poles) mounted on a stub bearing 214. A thin layer (e.g. 0.001"–0.002") of hermetic sealant, such as Parylene, is vapor deposited over the magnet to isolate the fluid being pumped from the magnet material. A shaft 216 extends axially from the rotor 204 and couples to a conventional gear pump head 206. (It will be recognized that a variety of pump mechanisms, other than gear pumps, can alternatively be used.)

The illustrated assembly 200 does not include a metal cup enclosure. Instead, the molded housing 208 is shaped to form an annular cavity 218 within which the stator windings and laminates are positioned. A cover piece 220 closes the cavity. Between the stator 202 and the rotor 204, the housing 208 forms a cylindrical wall 222 that serves the purpose of the steel cup enclosure in the prior art. That is, it isolates that stator 202 from the fluid being pumped, while forming a fluid-tight well 224 within which the rotor 204 can rotate.

Figure 7:
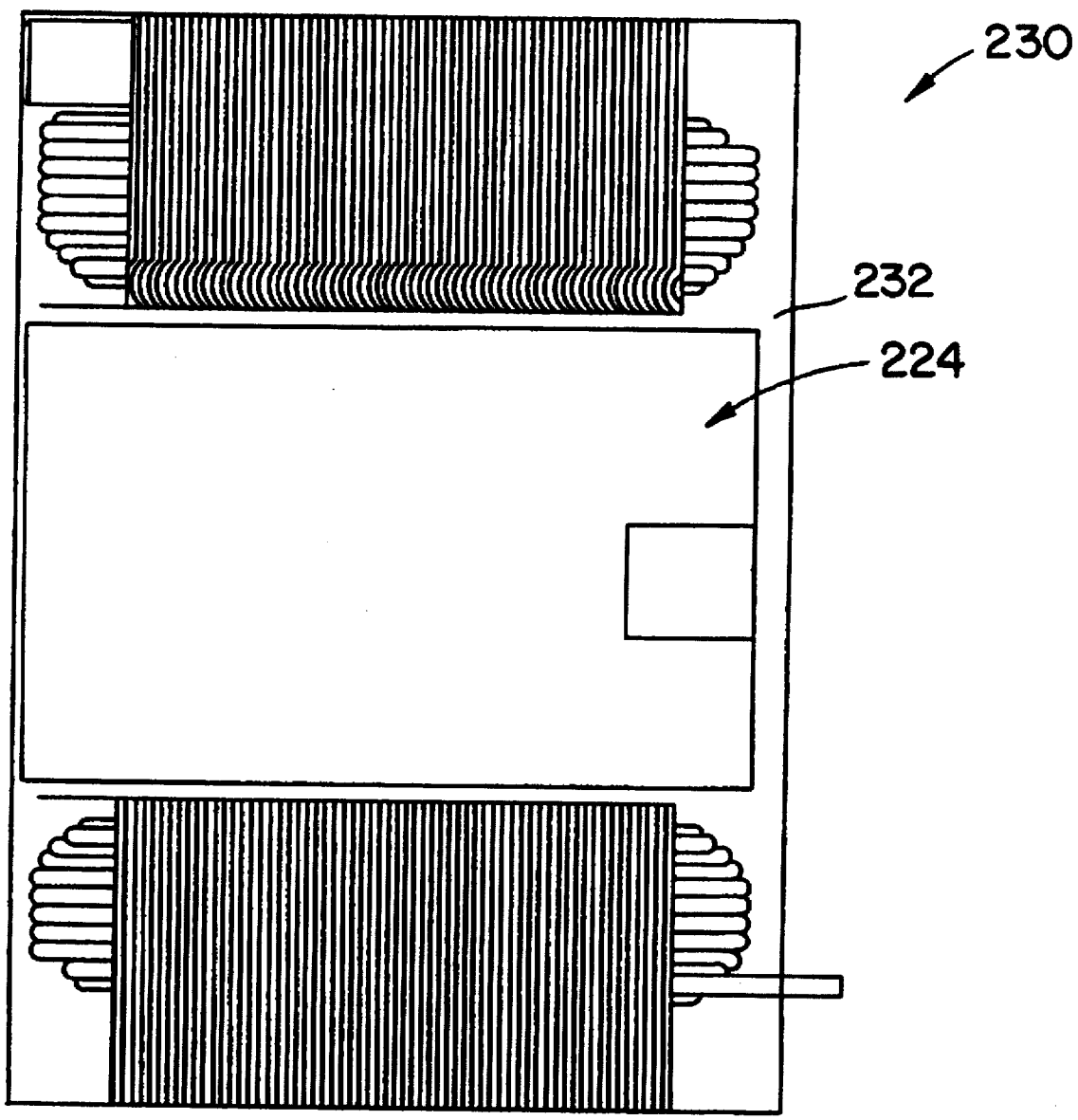
FIG. 7 shows an improved motor/pump assembly according to an embodiment of the invention.

A related embodiment 230 is shown in FIG. 7. In the FIG. 7 assembly, the two part housing (i.e. housing 208 and cover piece 220) are not used. Instead, the stator components are injection molded within a unitary plastic assembly 232 that encapsulates the stator and simultaneously defines the rotor well 224.

Desirably, the housings in both of the foregoing embodiments are formed of a high-temperature plastic that offers dimensional stability over a wide range of temperature extremes. Ryton is used in the illustrated embodiment. Adoption of this material, however, complicates fabrication due to its high melting temperature (e.g. 600° F.). Conventional solder melts below this temperature, so connections to the stator windings must be made with a higher temperature solder (e.g. silver solder), or implemented in crimp fashion.

The illustrated arrangements provide several advantages over the prior art. One is cost savings. The injection-molded plastic parts are inexpensive to fabricate, as contrasted with the expensive deep drawn steel cup enclosure of the prior art. The embodiment illustrated in FIG. 6 is less expensive because it has a molded housing 208 instead of the expensive steel cup. Using the molded housing arrangement, the stator-rotor gap is on the order of 0.085" In FIG. 7, the stator is injection molded within a unitary plastic assembly 232, which obviates the need for an expensive steel cup.

In addition to cost savings, the embodiment illustrated in FIG. 7 provides important functional advantages: improved torque and efficiency. While the stator-rotor gap in the steel cup design is on the order of 0.040" to 0.045", in the arrangement of FIG. 7, the gap is reduced to about 0.030" (0.020" for the wall thickness of the plastic 232/222, plus an air/fluid gap of about 0.010"). With this reduction in gap comes an attendant improvement in motor performance.

Having illustrated and described the principles of the invention in a preferred embodiment, it should be apparent to those skilled in the art that the invention can be modified in arrangement and detail without departing from such principles. We claim all modifications and equivalents coming within the spirit and scope of the following claims.

APPENDICES

Forming a part of the present specification is the following Appendix A, a program listing for motor controller.

U.S. Patent Application of Keith E. Chipperfield et al.

For: PUMP MOTOR AND MOTOR CONTROL

Atty. Ref. No.: 3316-42470

Serial No.: _____

Filing Date: _____

Express Mail Label No.: TB655394080US

APPENDIX A
"Program Listing for Motor Controller"

Title ' SEQUENCER PAL'
Designer ' KEITH CHIPPERFIELD'
Date ' 11/29/94'

Description
  Experimental PAL used to "step" BLDC motor for low speed operation.
End_Desc;

PEEL20CG10A

CLK_IN PIN 1

"I/O CONFIGURATION DECLARATION
"IOC (PIN_NO 'PIN_NAME' OUTPUT_POLARITY OUTPUT_TYPE
FEEDBACK_TYPE)
ILIMIT pin 2
IOC (14 'Q0' Pos OutReg Feed_Pin)
IOC (15 'Q1' Pos OutReg Feed_Pin)
IOC (16 'Q2' Pos OutReg Feed_Pin)
IOC (17 '' Pos OutCom Feed_Pin)
IOC (18 'LOWER_C' Pos OutCom Feed_Pin)
IOC (19 'LOWER_B' Pos OutCom Feed_Pin)
IOC (20 'LOWER_A' Pos OutCom Feed_Pin)
IOC (21 'UPPER_C' Pos OutCom Feed_Pin)
IOC (22 'UPPER_B' Pos OutCom Feed_Pin)
IOC (23 'UPPER_A' Pos OutCom Feed_Pin)

AC node 25
SP node 26

DEFINE

EQUATIONS

AC = 0;

SP = 0;

"All Equations must end with semicolons.
"Internal or External output names appended with extensions:
" 1) .COM for Combinatorial Output
" 2) .D for D-type Registered Output
" 3) .OE for Output Enable Control
Q0.And = 0;
Q0.D = !Q0 & !(Q0 & Q1 & Q2);

Q1.And = 0;
Q1.D = !Q1 & Q0
     # !Q0 & Q1
     # Q0 & Q1 & Q2;

Q2.And = 0;

Q2.D = !Q2 & Q0 & Q1 & !(Q0 & Q1 & Q2)
    # !(Q0 & Q1) & Q2 & !(Q0 & Q1 & Q2);

LOWER_C.And = 0;
LOWER_C.Com = !Q0 & Q1 & !Q2 & ILIMIT
    # Q0 & Q1 & !Q2 & ILIMIT;

LOWER_B.And = 0;
LOWER_B.Com = !Q0 & Q1 & Q2 & ILIMIT
    # Q0 & Q1 & Q2 & ILIMIT;

LOWER_A.And = 0;
LOWER_A.Com = !Q0 & !Q1 & Q2 & ILIMIT
    # Q0 & !Q1 & Q2 & ILIMIT;

UPPER_C.And = 0;
UPPER_C.Com = Q0 & !Q1 & Q2
    # !Q0 & Q1 & Q2;

UPPER_B.And = 0;
UPPER_B.Com = Q0 & Q1 & !Q2
    # !Q0 & !Q1 & Q2;

UPPER_A.And = 0;
UPPER_A.Com = !Q0 & Q1 & !Q2
    # Q0 & Q1 & Q2;

Description:-

Q0, Q1, and Q2 form a 3 bit counter that counts through six states:-

| Q2 | Q1 | Q0 |
|----|----|----|
| 0  | 1  | 0  |
| 0  | 1  | 1  |
| 1  | 0  | 0  |
| 1  | 0  | 1  |
| 1  | 1  | 0  |
| 1  | 1  | 1  |

The commutation sequences are driven from the 6 states of the counter as follows:-

| PHASE | COUNTER | UA | UB | UC | LA | LB | LC | GATE |
|-------|---------|----|----|----|----|----|----|------|
| 0     | 010     | 1  | 0  | 0  | 0  | 0  | 1  | 1    |
| 1     | 011     | 0  | 1  | 0  | 0  | 0  | 1  | 0    |
| 2     | 100     | 0  | 1  | 0  | 1  | 0  | 0  | 0    |
| 3     | 101     | 0  | 0  | 1  | 1  | 0  | 0  | 1    |
| 4     | 110     | 0  | 0  | 1  | 0  | 1  | 0  | 0    |
| 5     | 111     | 1  | 0  | 0  | 0  | 1  | 0  | 0    |

Title ' SEQUENCER PAL'
Designer ' KEITH CHIPPERFIELD'
Date ' 1/5/95'

Description
Experimental PAL used to "step" BLDC motor for low speed operation.
Reverse capability added 1/5/95. reversing is implemented by "swapping"
the Upper A & C and the Lower A & C terms. The switching of the upper
and lower B outputs remains unchanged.
End_Desc;

PEEL20CG10A

CLK_IN PIN 1

"I/O CONFIGURATION DECLARATION
"IOC (PIN_NO 'PIN_NAME' OUTPUT_POLARITY OUTPUT_TYPE
FEEDBACK_TYPE)
ILIMIT pin 2
REV pin 3
IOC (14 'Q0' Pos OutReg Feed_Pin)
IOC (15 'Q1' Pos OutReg Feed_Pin)
IOC (16 'Q2' Pos OutReg Feed_Pin)
IOC (18 'LOWER_C' Pos OutCom Feed_Pin)
IOC (19 'LOWER_B' Pos OutCom Feed_Pin)
IOC (20 'LOWER_A' Pos OutCom Feed_Pin)
IOC (21 'UPPER_C' Pos OutCom Feed_Pin)
IOC (22 'UPPER_B' Pos OutCom Feed_Pin)
IOC (23 'UPPER_A' Pos OutCom Feed_Pin)

AC node 25
SP node 26

DEFINE

EQUATIONS

AC = 0;

SP = 0;

"All Equations must end with semicolons.
"Internal or External output names appended with extensions:
" 1) .COM for Combinatorial Output
" 2) .D for D-type Registered Output
" 3) .OE for Output Enable Control
Q0.And = 0;
Q0.D = !Q0 & !(Q0 & Q1 & Q2);

Q1.And = 0;
Q1.D = !Q1 & Q0
    # !Q0 & Q1

```
         # Q0 & Q1 & Q2;

Q2.And = 0;
Q2.D = !Q2 & Q0 & Q1 & !(Q0 & Q1 & Q2)
     # !(Q0 & Q1) & Q2 & !(Q0 & Q1 & Q2);

LOWER_C.And = 0;
LOWER_C.Com = !Q0 & Q1 & !Q2 & ILIMIT & !REV
     # Q0 & Q1 & Q2 & ILIMIT & !REV
     # !Q0 & !Q1 & Q2 & ILIMIT & REV
     # Q0 & !Q1 & Q2 & ILIMIT & REV;

LOWER_B.And = 0;
LOWER_B.Com = !Q0 & Q1 & Q2 & ILIMIT
     # Q0 & Q1 & Q2 & ILIMIT;

LOWER_A.And = 0;
LOWER_A.Com = !Q0 & !Q1 & Q2 & ILIMIT & !REV
     # Q0 & !Q1 & Q2 & ILIMIT & !REV
     # !Q0 & Q1 & !Q2 & ILIMIT & REV
     # Q0 & Q1 & !Q2 & ILIMIT & REV;

UPPER_C.And = 0;
UPPER_C.Com = Q0 & !Q1 & Q2 & !REV
     # !Q0 & Q1 & Q2 & !REV
     # !Q0 & Q1 & !Q2 & REV
     # Q0 & Q1 & Q2 & REV;

UPPER_B.And = 0;
UPPER_B.Com = Q0 & Q1 & !Q2
     # !Q0 & !Q1 & Q2;

UPPER_A.And = 0;
UPPER_A.Com = !Q0 & Q1 & !Q2 & !REV
     # Q0 & Q1 & Q2 & !REV
     # Q0 & !Q1 & Q2 & REV
     # !Q0 & Q1 & Q2 & REV;
```

We claim:

1. A pump motor controller for controlling pump motor speed independent of external pressures on the pump, comprising:
   a reference input to enable direct control of speed of a pump motor;
   commutation sensors for determining the speed of the pump motor;
   a comparator coupled to the commutation sensors and the reference input for producing an output signal based on a comparison between the pump motor speed and the reference input; and
   a drive circuit including a forward drive amplifier coupled to the comparator for receiving the output signal and providing a forward drivel signal proportional to forward drive, a reverse drive amplifier coupled to the comparator for receiving the output signal and providing a reverse drive signal proportional to reverse drive, the drive circuit coupled to the comparator for commutating the pump motor in forward to increase the speed of the pump motor in response to the forward drive signal and for commutating the pump motor in reverse in response to the reverse drive signal to brake the speed of the pump motor such that the speed of the pump motor converges to the reference input.

2. The pump motor controller of claim 1 wherein the comparator comprises a phase comparator of a phase locked loop circuit.

3. The pump motor controller of claim 1 further comprising:
   a frequency discriminator for sensing the reference input and for causing the drive circuit to commutate the pump motor in reverse when the reference input falls below a threshold value; and
   a reverse movement detector for sensing reverse movement of the pump motor and for deactivating the drive circuit when reverse movement occurs.

4. The pump motor controller of claim 1, wherein the reference input is a control frequency.

5. The pump motor controller of claim 1, wherein the reference input is a control voltage.

6. The pump motor controller of claim 5, wherein the reference input further includes a control frequency.

7. A pump motor controller for a brushless D.C. motor, comprising:
   a reference input;
   commutation sensors for determining speed of the motor;
   a phase comparator coupled to the commutation sensors and the reference input for comparing the speed of the motor with the reference input, and for providing an output voltage based on a comparison of the speed of the motor and the reference input; and
   a drive circuit coupled to the comparator for receiving the output voltage and for commutating the motor forward to increase the speed of the motor and commutating the motor in reverse to decrease the speed of the motor so that the speed of the motor converges to the reference input.

8. The pump motor controller of claim 7, wherein the reference input is a control frequency or a control voltage.

9. A pump motor controller for a brushless D.C. motor, comprising:
   a reference input for controlling motor speed;
   commutation sensors for determining motor speed;
   a phase locked loop circuit, coupled to the reference input and the commutation sensors, for comparing the motor speed with the reference input and producing an output voltage based on a phase comparison of the motor speed and the reference input; and
   a drive circuit coupled to the phase locked loop circuit for commutating the motor forward to increase the speed of the motor and communicating the motor in reverse to decrease the speed of the motor so that the speed of the motor converges to the reference input.

10. The pump motor controller of claim 9, wherein the reference input includes a signal providing a control frequency.

11. The pump motor controller of claim 9, wherein a voltage controlled oscillator converts a D.C. input voltage to an oscillating voltage having a frequency proportional to the magnitude of the D.C. voltage, and the oscillating voltage provides the reference input.

12. A pump motor controller for a brushless D.C. motor, comprising:
   a reference input;
   commutation sensors for determining speed of the motor;
   a phase comparator coupled to the commutation sensors and the reference input for comparing the speed of the motor with the reference input, and for providing an output voltage based on a comparison of the speed of the motor and the reference input;
   a drive circuit coupled to the comparator for driving the motor by commutation at a speed and direction depending on the magnitude of the output voltage;
   a frequency discriminator for sensing the reference input and for causing the drive circuit to commutate the motor in reverse when the reference input falls below a threshold value; and
   a reverse movement detector for sensing reverse movement of the motor and for stopping reverse commutation of the motor by the drive circuit when reverse movement occurs.

13. A pump motor controller for a brushless D.C. motor, comprising:
   a reference input for controlling motor speed;
   commutation sensors for determining motor speed;
   a phase locked loop circuit, coupled to the reference input and the commutation sensors, for comparing the motor speed with the reference input and producing an output voltage based on a phase comparison of the motor speed and the reference input; and
   a drive circuit coupled to the phase locked loop circuit for increasing or decreasing motor speed based on the magnitude of the output voltage such that the motor speed converges to the reference input wherein the drive circuit employs reverse commutation to decrease motor speed when the motor speed exceeds the frequency of the reference input.

14. A pump motor controller for a brushless D.C. motor, comprising:
   a reference input for controlling motor speed;
   commutation sensors for determining motor speed;
   a phase locked loop circuit, coupled to the reference input and the commutation sensors, for comparing the motor speed with the reference input and producing an output voltage based on a phase comparison of the motor speed and the reference input;
   a drive circuit coupled to the phase locked loop circuit for increasing or decreasing motor speed based on the magnitude of the output voltage such that the motor speed converges to the reference input;

a frequency discriminator for sensing the reference input and for causing the drive circuit to commutate the motor in reverse when the reference input falls below a threshold value; and a reverse movement detector for sensing reverse movement of the motor and for stopping reverse commutation of the motor by the drive circuit when reverse movement occurs.

15. A pump motor controller for a brushless D.C. motor, comprising:

a reference input;

commutation sensors for determining speed of the motor;

a comparator coupled to the commutation sensors and the reference input for comparing the speed of the motor with the reference input, and for providing an output voltage based on a comparison of the speed of the motor and the reference input;

a drive circuit coupled to the comparator for driving the motor by commutation at a speed and direction depending on the magnitude of the output voltage;

a frequency discriminator for sensing the reference input and for causing the drive circuit to commutate the motor in reverse when the reference input falls below a threshold value; and a reverse movement detector for sensing reverse movement of the motor and for stopping reverse commutation of the motor by the drive circuit when reverse movement occurs.

16. A pump motor controller for controlling pump motor speed independent of external pressures on the pump, comprising:

a reference input to enable direct control of speed of a pump motor;

commutation sensors for determining the speed of the pump motor;

a comparator coupled to the commutation sensors and the reference input for producing an output signal based on a comparison between the pump motor speed and the reference input;

a drive circuit coupled to the comparator for receiving the output signal and for commutating the pump motor in forward or reverse depending on information conveyed in the output signal;

a frequency discriminator for sensing the reference input and for causing the drive circuit to commutate the pump motor in reverse when the reference input falls below a threshold value; and a reverse movement detector for sensing reverse movement of the pump motor and for deactivating the drive circuit when reverse movement occurs.

* * * * *

UNITED STATES PATENT AND TRADEMARK OFFICE
CERTIFICATE OF CORRECTION

PATENT NO. : 5,670,852

DATED : September 23, 1997

INVENTOR(S) :
Keith E. Chipperfield

It is certified that error appears in the above-identified patent and that said Letters Patent is hereby corrected as shown below:

On the title page: Item [75] delete all inventors except "Keith E. Chipperfield".

Column 2, line 60, "controller allows" should read --controller that allows--.

Column 3, line 18, "input,." should read --input,--.

Column 3, line 24, "the' stator" should read --the stator--.

Column 9, line 31, "remove" should read --move--.

Column 11, line 27, "5, Frequency" should read --5 * Frequency--.

Column 12, line 31, "in a the stator" should read --in the stator--.

Column 14, line 31, "0.085" In" should read --0.085". In--.

Column 25, line 15, "drivel signal" should read --drive signal--.

Column 26, line 6, "communicating" should read --commutating--.

Signed and Sealed this

Thirtieth Day of March, 1999

Attest:

Q. TODD DICKINSON

*Attesting Officer*

*Acting Commissioner of Patents and Trademarks*